United States Patent [19]
Lund et al.

[11] Patent Number: 4,911,014
[45] Date of Patent: Mar. 27, 1990

[54] METHOD OF ANALYZING AND EVALUATING THE RESULTS OF AN ULTRASONIC EXAMINATION

[75] Inventors: Svend A. Lund, Birker d; Willy D. Kristensen; Bent E. Nielsen, both of Lyngby, all of Denmark

[73] Assignee: Akademiet For De Tekniske Videnskaber, Svejsecentralen, Brondby, Denmark

[21] Appl. No.: 223,014

[22] Filed: Jul. 22, 1988

[51] Int. Cl.⁴ ............................................. G01N 29/04
[52] U.S. Cl. .......................................... 73/602; 73/619
[58] Field of Search ................. 73/602, 614, 619, 627, 73/629; 382/50, 51

[56] References Cited

U.S. PATENT DOCUMENTS

| | | | |
|---|---|---|---|
| 3,939,697 | 2/1976 | Lund et al. | 73/614 |
| 4,226,122 | 10/1980 | Lund et al. | 73/620 |
| 4,292,848 | 10/1981 | Rainey et al. | 73/602 |
| 4,495,816 | 1/1985 | Schlumberger | 73/602 |
| 4,531,409 | 7/1985 | Koch et al. | 73/602 |

Primary Examiner—Hezron E. Williams
Assistant Examiner—Louis M. Arana
Attorney, Agent, or Firm—Banner, Birch, McKie & Beckett

[57] ABSTRACT

A prior art computerized ultrasonic examination is first performed by moving an ultrasonic probe over the surface of an object, emitting short pulses of ultrasonic energy into the material. Combined digital position and echo pulse signals are electronically stored, processed and used for the display of video images presenting accumulated echo amplitude data in circular patterns associated with selected sectional planes through the object. The results of the examination are then analyzed and evaluated by means of a mathematical model, able to produce imaginary digital data simulating the progression and reflection of sound pulses emitted by the ultrasonic probe. Imaginary echo signals from imaginary point reflection sources corresponding to selected individual flaw image pixels are then compared with the actual echo pulse signals electronically stored, and in cases of identical sound path lengths, the corresponding actual echo pulse signals are deleted from the memory. By such successive elimination of individual flaw echo signals from the totality of echo signals received, it becomes possible to analyze complex flaw combinations in successively revised sectional images, removing individual flaw images one by one. The peak amplitude values of deleted echo pulse signals may further be re-stored, processed and used for the display of video sectional and projection flaw images of drastically improved quality and precision.

3 Claims, 4 Drawing Sheets

METHOD OF ANALYZING AND EVALUATING THE RESULTS OF AN ULTRASONIC EXAMINATION

BACKGROUND OF THE INVENTION

1. Field of the Invention

This invention relates to the analysis and evaluation of the results of ultrasonic examinations by the pulse-echo method of solid objects having a plane or locally substantially plane surface. The correct location, interpretation and sizing of internal flaws in materials and welded joints are matters of the greatest importance for the safety and fitness for purpose of important structures and installations.

2. Background of the Prior Art

In the ultrasonic examination art, great efforts have been made to develop improved systems for the location and sizing of flaws in materials and welded joints, in particular systems producing easily readable images of internal flaws. In many systems this has been made possible through the use of digital computing means including electronic matrix memories for the storage of echo data which may then be analysed, displayed on video monitors as grey scale or colour images, and permanently recorded by magnetic recording means or permanent prints.

In a previous patent application, WO, Lund et al., 87/07026, we have disclosed a system for ultrasonic examination providing sectional and projection views showing flaw images of greatly improved precision and sharpness of definition.

According to said previous invention, at least one ultrasonic probe is moved over the surface of the object examined in steps of predetermined lengths along a rectilinear scanning path containing the projection on the surface of the central axis of the sound beam; position signal producing means is adapted to produce digital signals containing information on the position on said surface of the successive points of incidence of the sound beam; ultrasonic equipment is adapted to make said probe emit, on completion of each step of movement, at least one short pulse of ultrasonic energy into the object, and adapted, on receipt of an echo pulse, to produce digital echo signals containing information on the amplitude of said pulse, and on the length of the sound path from said point of incidence to the reflecting point causing the echo pulse; digital computing means is provided, including a first electronic matrix memory for data produced by the examination, said first matrix memory having storage addresses arranged in lines and columns associated with a similar, corresponding network of lines and columns of rectangular co-ordinates in the section plane through the object defined by the scanning path of the ultrasonic probe and the central axis of the sound beam, each storage address being adapted to store data representing said echo amplitudes, and adapted, on receipt of a new data item, to add said new data item to the sum of data items previously stored at said storage address; first control means is provided for storing in said first matrix memory, upon receipt of said position signal and said echo pulse signals, data representing said echo amplitude at all storage addresses located on a circle, having as its centre the storage address associated with said point of incidence, and having as its radius the distance in said first matrix memory corresponding to said length of the sound path through the object; a video screen terminal is provided for controlling the scanning movement of said ultrasonic problem, for controlling the functioning of said ultrasonic equipment, said digital computing means, and said first control means, and for displaying sectional images derived from data stored in said first matrix memory; recording means is provided for producing permanent, electronically readable records of data stored in said first matrix memory, and of sectional images displayed on said screen terminal; and printing means is provided for producing permanent prints of images displayed on said screen terminal.

According to said previous invention, said ultrasonic probe can further be moved over the surface of the object along a number of successive, parallel rectilinear scanning paths at predetermined intervals; said digital computing means then further includes at least one further matrix memory having storage addresses arranged in lines and columns associated with a similar, corresponding network of lines and columns of rectangular co-ordinates in a projection plane parallel to or at right angles to the surface of the object examined, each storage address being adapted to store sums of data items representing said echo amplitudes; further control means is then adapted, on completion of each movement of said ultrasonic probe along the length of a scanning path, to read from the storage addresses of said first matrix memory the highest sums of data items stored in each line or column, to store said highest sums of data items at the corresponding storage addresses in a line or column in said further matrix memory, and to reset all storage addresses in said first matrix memory at zero value; said video screen terminal is then further adapted to control the functioning of said further control means, and to display projection images derived from data stored in said further matrix memory; and said recording means is then further adapted to produce permanent, electronically readable records of data stored in said further matrix memory.

The system according to said previous invention, providing accumulated storage of echo amplitude data values at memory locations corresponding to the actual positions of internal flaws, has in practical examinations led to a drastic increase in the quality and precision of sectional and projection flaw images in comparison with prior art systems, in particular in cases where only one internal flaw has been present in the object examined.

The system has, however, not been entirely satisfactory in cases where a number of internal flaws of different significance have been present in the same sectional plane. The high echo amplitude data values stored in the circular patterns intersecting at the location of a more significant reflector show a tendency to overshadow the lower echo amplitude data values stored at the locations of less significant reflectors, making it difficult or impossible to analyse and evaluate the aggregate flaw images in a correct manner.

SUMMARY OF THE INVENTION

The method according to the present invention has been evolved with the object of overcoming the disadvantages of the prior art by providing a new and satisfactory method of analysing and evaluating the results of an ultrasonic examination which has produced flaw images showing complex and overlapping patterns of echo data amplitude values.

According to the invention, there is first performed a prior art ultrasonic examination comprising the steps of moving at least one ultrasonic probe over the surface of the object to be examined, making said probe emit, at predetermined intervals of time, one short pulse of ultrasonic energy into the object; producing at each emission of an ultrasonic pulse, digital position signals containing information on the corresponding position of the point of incidence and central axis direction of the sound beam in a predetermined three-dimensional system of co-ordinates in fixed relation to the object; producing by means of ultrasonic equipment, on receipt of an echo pulse, digital echo signals containing information on the amplitude of said echo pulse, and on the length of the sound path from said point of incidence to the reflecting point causing said echo pulse; storing by digital computing means, connected values of said echo and position signals in a first electronic memory; selecting for study a sectional plane through the object examined, defining in said sectional plane a two-dimensional system of rectangular co-ordinates in known relation to said three-dimensional system of co-ordinates in the object examined; determining for each echo pulse received, the circular curve of intersection, if any, between said sectional plane and a sphere having its centre at the corresponding point of incidence of the sound beam and having as its radius the length of the sound path from said point of incidence to the reflecting point causing said echo pulse; storing said echo signals by digital computing means in a second electronic matrix memory having storage addresses arranged in lines and columns associated with a corresponding network of lines and columns in said two-dimensional system of co-ordinates, each storage address being adapted to store data representing said echo amplitudes, and adapted, on receipt of a new data item, to add said new data item to the sum of data items previously stored at said storage address, by storing data representing each echo amplitude at all storage addresses located on the circle in said second matrix memory corresponding to said circular curve of intersection in said sectional plane; and displaying by means of a video screen monitor, a video sectional image derived from the accumulated data stored in said second matrix memory, showing indications of inhomogeneities, if any, found in said sectional plane through the object examined.

According to the invention, there is then provided a method of analysing and evaluating the results of the ultrasonic examination, comprising the steps of establishing by digital computing means, a digital mathematical model simulating the shape, amplitude, directivity and progression of a sound pulse emitted by said ultrasonic probe from a selected imaginary point of incidence, said mathematical model being able to produce imaginary digital echo pulse signals from a selected imaginary point reflection source in the object examined, said imaginary pulse signals containing information on the amplitude of said imaginary echo pulse, and on the length of the sound path from said imaginary point of incidence of said imaginary point source causing said imaginary echo pulse; selecting from said video sectional image of inhomogeneities found in the object examined, a first image pixel at or near the flaw image of a first inhomogeneity; introducing into said mathematical model a first imaginary point reflection source at the co-ordinates in the object examined corresponding to said selected first image pixel; introducing into said mathematical model a first combination of a first imaginary point of incidence and a first central axis direction of the sound beam, selected from among the combinations of actual position signals stored in said first electronic memory; comparing the imaginary echo pulse signal obtained by said mathematical model with the corresponding actual echo pulse signals stored in said first electronic memory having amplitude values exceeding a predetermined threshold value; deleting, in case of identical path lengths indicated by said imaginary and said actual echo pulse signals, said actual echo pulse signals from said first electronic memory; successively introducing into said mathematical model the further combinations of points of incidence and central axis directions of the sound beam stored in said first electronic memory, and, for each selected combination, repeating the comparing and deleting procedures disclosed above in relation to said first combination; producing a revised second video sectional image of inhomogeneities found ins aid sectional plane, derived from the remaining data stored in said first electronic memory, using the same procedure as disclosed above in relation to said first video sectional image; successively selecting further image pixels remaining at or near the flaw image of said first inhomogeneity, and, for each selected image pixel, repeating the introduction into said mathematical model of a corresponding imaginary point reflection source, the successive introduction of the combinations of points of incidence and central axis directions of the sound beam stored in said first electronic memory, and, for each selected combination, the comparing and deleting procedures disclosed above in relation to said first image pixel, repeating said production of revised video sectional images and said selection of image pixels, until all echo signals contributing to the flaw image of said first inhomogeneity having amplitude values exceeding a predetermined threshold value have been eliminated from the totality of echo signals obtained during the examination of the object in question; and successively selecting from revised sectional images, further flaw images of imhomogeneities found in said sectional plane through the object examined, repeating the echo signal elimination procedures disclosed above in relation to said first inhomogeneity, until all echo signals contributing to flaw images in said revised video sectional images having amplitude values exceeding a predetermined threshold value have been eliminated from the totality of echo signals obtained during the examination of the object in question.

By the method disclosed by the present invention, comprising the systematic, successive elimination of individual flaw echo signals from the totality of echo signals obtained during an ultrasonic examination, it has become possible to perform a correct and exact analysis and evaluation in detail of complex and overlapping patterns of flaw echo data. When dominant echo amplitude data values from more significant reflectors have been selectively deleted from the electronic memory, it becomes possible to study in a correct manner also less significant reflectors present in the object examined.

According to the invention, additional improvements in the analysis and evaluation of selected, individual inhomogeneities detected by an ultrasonic examination can be obtained by the further step of storing by digital computing means, each time an actual echo pulse signal has been deleted from said first electronic memory, data representing the peak amplitude of said actual echo pulse signal at the storage address corresponding to the image pixel selected for elimination, in a third electronic matrix memory identical with said second electronic matrix memory and having storage addresses similarly adapted to store accumulated data representing echo amplitudes; and displaying by means of a video screen monitor, a revised video sectional image derived from the accumulated data stored in said third matrix memory, indicating echo information exclusively related to said selected inhomogeneity.

By the additional steps disclosed by the present invention, it has further become possible to produce and record sectional flaw images (B-scan displays) of a hitherto unknown precision and sharpness of definition, including correct presentations of more significant as well as less significant reflector images at their respective exact locations in the selected sectional plane through the object examined.

According to the invention, extended analysis and evaluation of selected individual inhomogeneities detected by an ultrasonic examination can be obtained by the further steps of selecting a number of parallel sectional planes through the object examined, at predetermined mutual distances; storing by digital computing means, for each selected sectional plane, data representing the peak amplitudes of deleted actual echo pulse signals originating from inhomogeneities found in the object examined; and displaying at least one video projection image on a selected projection plane in known relation to the object examined, said projection image being derived from the totality of peak amplitude data stored in relation to said parallel sectional planes.

By such further steps disclosed by the present invention, it has become possible to produce and record projection flaw images (P-scan plan, side or end view displays) of hitherto unknown precision and sharpness of definition, permitting correct and precise location and evaluation of all internal inhomogeneities in three dimensions.

Other objects and advantages of the invention will be readily apparent from the following description taken in conjunction with the accompanying drawings.

DETAILED DESCRIPTION OF THE ILLUSTRATED EMBODIMENT

Figure 1:
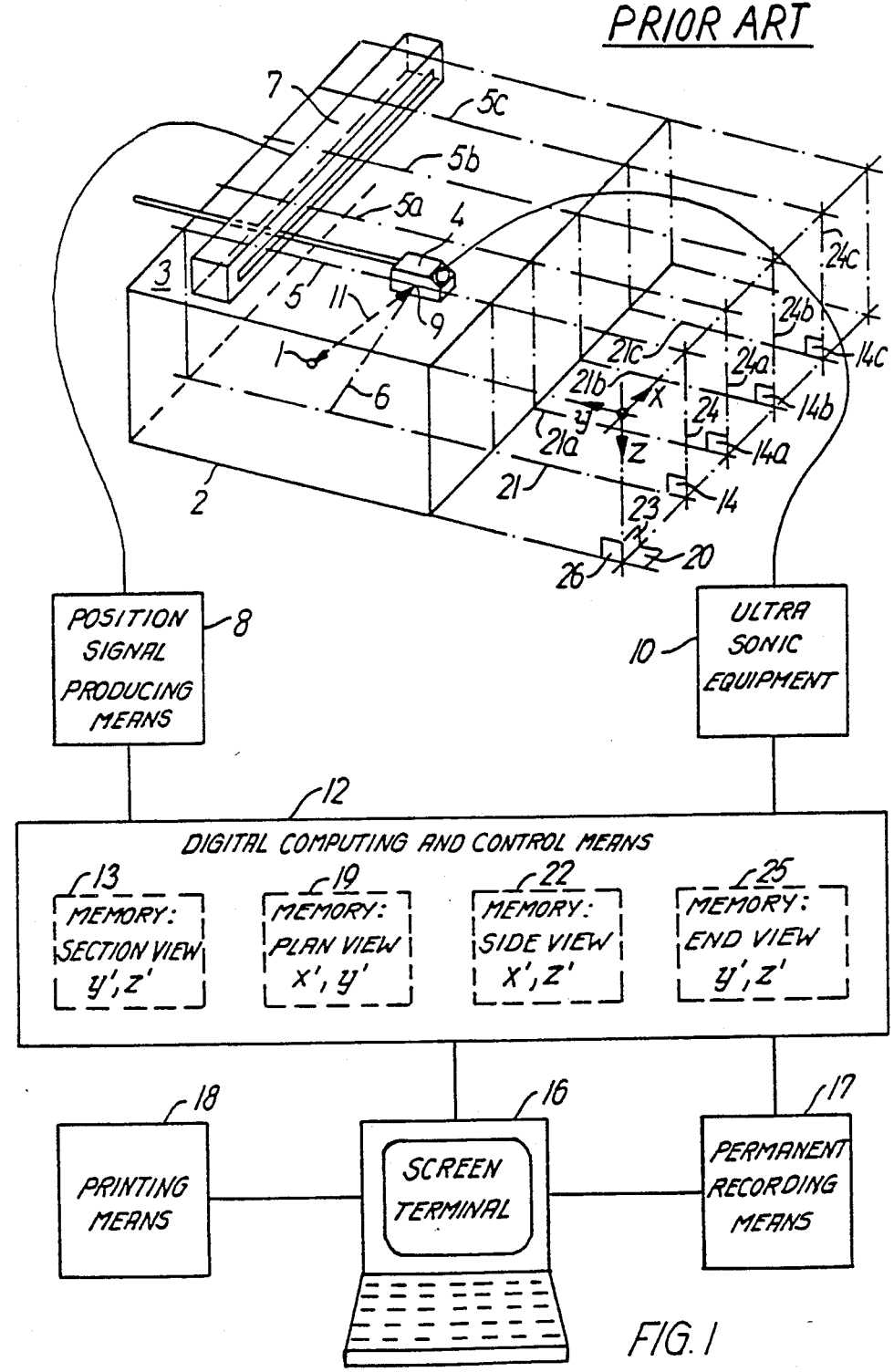
FIG. 1 is a schematic presentation partly as an isometric view, and partly as a block diagram, of a prior art ultrasonic examination system, constituting the background of the present invention.

FIG. 1 shows schematically a prior art ultrasonic examination system for producing and recording images of inhomogeneities 1 in an object 2 having a plane surface 3. An ultrasonic probe 4 is moved along a scanning path 5, emitting short pulses of ultrasonic energy into the object in a sound beam having a central axis 6. Position signal producing means 7,8 is adapted to transmit digital signals containing information on the positions of successive points of incidence 9 in a system of co-ordinates (x,y,z) in fixed relation to the object. On receipt of an echo pulse, an ultrasonic equipment 10 produces digital echo signals containing information on the amplitude of the echo pulse, and on the length of the sound path 11 from the point of incidence 9 to the reflecting point 1.

Connected position and echo pulse signals are carried to digital computing and control means 12 including one or more electronic matrix memories 13, 19,22,25 for data produced by the examination. A video screen terminal 16 controls the scanning movement of the ultrasonic probe and the functioning of the ultrasonic equipment and the digital computing and control means 12, and displays images derived from data stored in the matrix memories 13,19,22,25. Recording means 17 is provided for producing permanent, electronically readable records of the data stored in the matrix memories, and of images displayed on the screen terminal 16. Printing means 18 is provided for producing permanent prints of images displayed on the screen terminal.

Figure 2:
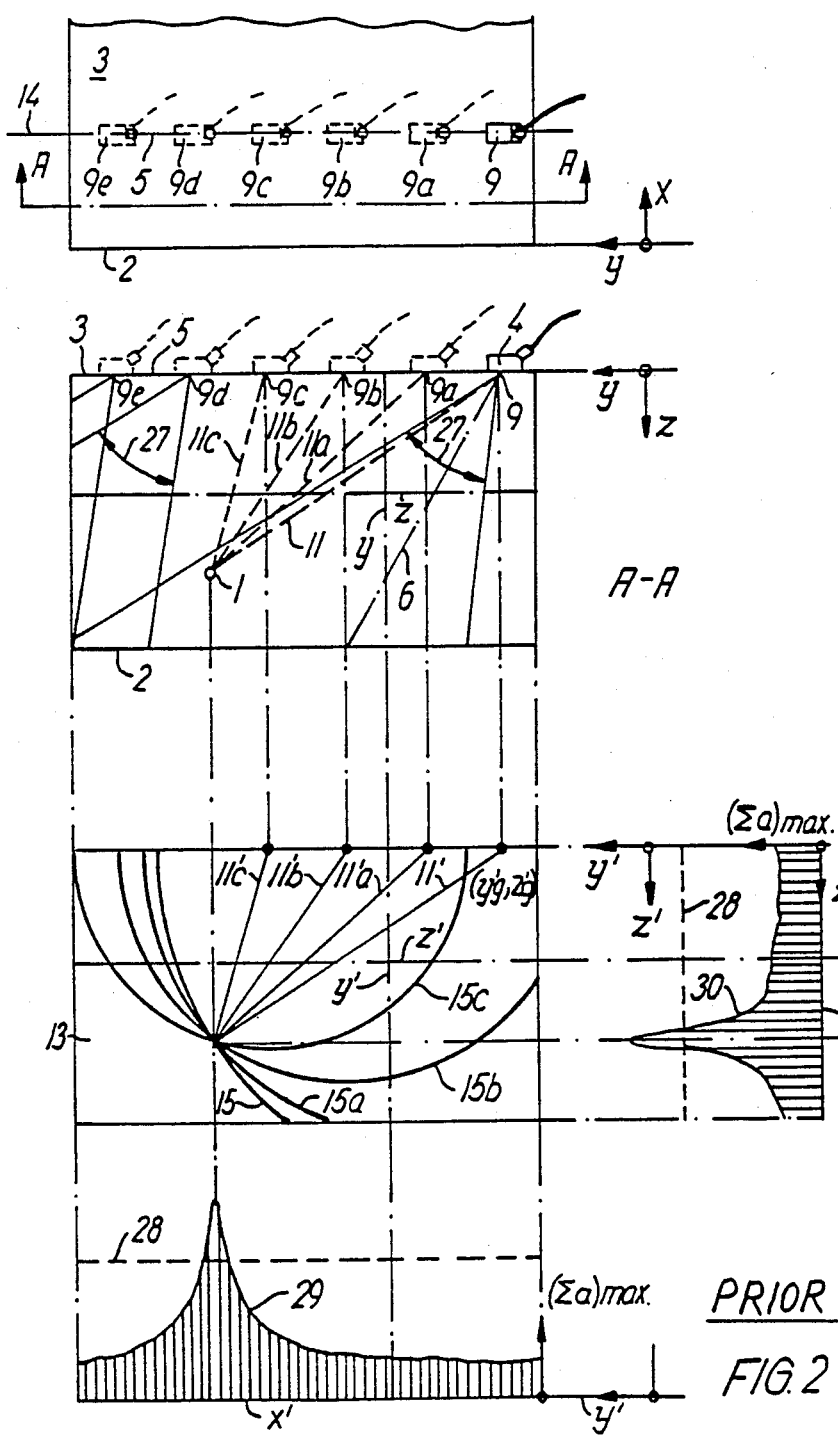
FIG. 2 is a schematic presentation of the production and storage of a sectional image (B-scan, display) by means of the prior art system of FIG. 1.

FIG. 2 further illustrates schematically the operation of the prior art examination system when producing an image (B-scan display) of a sectional plane 14 through the object 2. The matrix memory 13 has storage addresses $(x',z')$ arranged in lines $z'$ and columns $y'$ associated with a similar, corresponding network of lines $z$ and columns 7 of rectangular co-ordinates $(y,z)$ in the sectional plane 14. Each storage address $(y',z')$ is adapted to store data representing echo amplitudes (a), and adapted, on receipt of a new data item, to add the new data item (a) to the sum of data items ($\Sigma a$) previously stored at the same storage address.

Control means included in the digital computing means 12 is adapted, upon receipt of connected position and echo pulse signals, to arrange for the simultaneous storage in the matrix memory 13 of data representing the echo amplitude (a) at all storage addresses $(y',z')$ located on a circle 15, having as its centre the storage address $(y_9',z_9')$ associated with the corresponding point of incidence 9 of the sound beam, and having as its radius the distance 11' in the matrix memory 13 which corresponds to the length of the sound path 11 from the point of incidence 9 to the reflecting inhomogeneity inside the object.

The probe 4 is moved over the surface of the object to successive positions $9,9a,9b,\ldots 9e$. For each position, data representing echo pulse amplitudes, if any, are stored along the corresponding circle 15, 15a, 15b,15c in the matrix memory 13. On completion of the scanning movement, the accumulated sums of data items ($\Sigma a$) in the matrix memory can now be transformed into a proportional display of a complete sectional image on the video screen of the terminal 16. This transfer may include one or more of several well-known techniques of digital image processing, such as image filtering, contrast enhancement, grey scale or colour presentations, and the sectional image may be limited to include only stored sums of data items ($\Sigma a$) which are higher than an optional display threshold value 28.

The prior art system can, in relation to the present invention, be extended to permit a completely free movement and rotation of the probe 4 over the surface of the object, and a free selection for study of any sectional plane 14 through the object. Short pulses of ultrasonic energy are then emitted at predetermined intervals of time, and at each emission of an ultrasonic pulse, connected values of position and echo pulse signals, including the central axis direction of the sound beam in the system of co-ordinates (x,y,z), are stored by the digital computing means 12 in a first electronic memory (not shown).

In this latter case, each circular pattern of amplitude data stored in the second matrix memory 13 is replaced by the circular pattern corresponding to the circular curve of intersection, if any, between the sectional plane 14 and a sphere having its centre at the corresponding point of incidence of the sound beam and having as its radius the length of the sound path 11 from the point of incidence 9 to the reflecting point 1 causing the echo pulse.

The prior art system described may further be extended to be able to produce projection flaw images on one or more projection planes 20,23,26 at right angles to each other as indicated schematically in FIG. 1. A number of parallel sectional planes 14,14a,14b,14c is selected at predetermined mutual distances. For each selected sectional plane at a time, data representing echo pulse amplitudes are stored in the matrix memory 13 as described above and indicated schematically in FIG. 2. Further control means included in the digital computing means 12 is then adapted to read from the memory 13 the highest sums of data items $((\Sigma a)_{max})$ 29,30 stored in each line z' and column y', to transfer these highest sums of data items 29,30 to the corresponding storage addresses in the appropriate lines 21,21a,21b,21c or columns 24,24a,24b,24c in one or more further matrix memories 19,22,25, each memory being associated with a selected projection plane 20,23,26, and to reset all storage addresses in the memory 13 at zero value. The screen terminal 16, the recording means 17 and the printing means 18 are then adapted to display, record and print projection flaw images derived from the data stored in each of the matrix memories 19,22,25.

The prior art system for ultrasonic examination described above has in practice led to improved quality and precision of sectional and projection flaw images, in particular in cases as shown in FIG. 2, when only one internal flaw is present in the object examined, and when the flaw images are derived only from amplitude data values exceeding an appropriately high display threshold limit 28.

The system has, however, not been entirely satisfactory in cases where a number of internal flaws of different significance have been present in the same sectional plane. An example of such a case has been illustrated in FIG. 3. In this case, the matrix memory 13 contains a complex pattern of stored accumulated amplitude data, due to the presence of three different inhomogeneities in the same sectional plane through the object examined. The high echo amplitude data values stored in the circular patterns intersecting at the location 31 of a more significant reflector show a tendency to overshadow the lower echo amplitude data values stored at the locations 32,33 of two less significant reflectors. This tendency is even more clearly shown by the curve 34, indicating the highest sums of amplitude data $((\Sigma z)_{max})$ stored in the lines z' of the matrix memory 13, and the curve 35, indicating the highest sums of amplitude data $((\Sigma a)_{max})$ stored in the columns y' of the matrix memory 13. Whatever display threshold limit 28 is chosen, it is impossible to produce satisfactory images of the two less significant reflectors.

In such cases it is difficult or impossible by the prior art method to analyse and evaluate the aggregate flaw images in a correct manner, and it is the object of the present invention to provide a new and satisfactory method of analysing and evaluating the results of an ultrasonic examination which has produced flaw images showing such complex and overlapping echo amplitude data values.

The first step of the invented method is to establish by digital computing means, an auxiliary digital mathematical model simulating the shape, amplitude, directivity and progression of a sound pulse emitted by the ultrasonic probe 4 from a selected imaginary point of incidence on the surface 3 of an object 2. This mathematical model must further be able to produce imaginary echo pulse signals from any selected point reflection source inside the object 2, and the echo pulse signals must contain information on the amplitude of the imaginary echo pulse, and on the length of the sound path from the imaginary point of incidence to the imaginary point reflection source causing the imaginary echo pulse.

The establishment of digital mathematical models of this kind is wholly within the province of persons skilled in the art of ultrasonic examination and in the art of computer programming. Models of this kind can be designed in several different manners depending on the precision wanted, from quite simple models based on simplified general assumptions, to highly sophisticated models based on exact measurements and specific assumptions taking into consideration all known factors regarding the velocity, frequency, attenuation and dispersion losses, etc., of the ultrasonic waves, and regarding the specific properties of the ultrasonic probes used in the examination.

Referring to the example illustrated in FIG. 3, the invented method is then performed in the following manner:

From a video sectional image proportional to the storage patterns in the second matrix memory 13, a first image pixel is selected at or near the flaw image of the inhomogeneity at the location 21, and an imaginary point reflection source is introduced into the mathematical model at the co-ordinates (x,y,z) in the object 2 corresponding to the image pixel selected. At the same time, a first combination of an imaginary point of incidence and a central axis direction of the sound beam is introduced into the mathematical model, selected from among the combinations of actual position signals stored in the first electronic memory.

The imaginary echo pulse signals produced by the mathematical model are then compared with the corresponding actual echo pulse signals stored in the first electronic memory having amplitude values exceeding a predetermined noise threshold value, and if identical path lengths are indicated by the imaginary and the actual echo pulse signals, then the actual echo pulse signals are deleted from the first electronic memory.

Retaining the selected imaginary point reflection source, all the further combinations of points of incidence and central axis directions stored in the first electronic memory are then successively introduced into the mathematical model, and for each selected combination, comparing and deleting procedures are performed as described above in relation to the selected first combination.

A revised video sectional image is now produced, derived from a revised storage pattern in the second matrix memory 13 produced by the remaining data stored in the first electronic memory. This revised image will then show that one or more of the circular storage patterns intersecting at the location 31 have now been eliminated from the image.

In the revised video sectional image, it is then possible to select further image pixels, one at a time at or near the location 31, repeating for each image pixel the eliminating procedure described above in relation to the selected first image pixel, and the display of a revised video sectional image.

Figure 4:
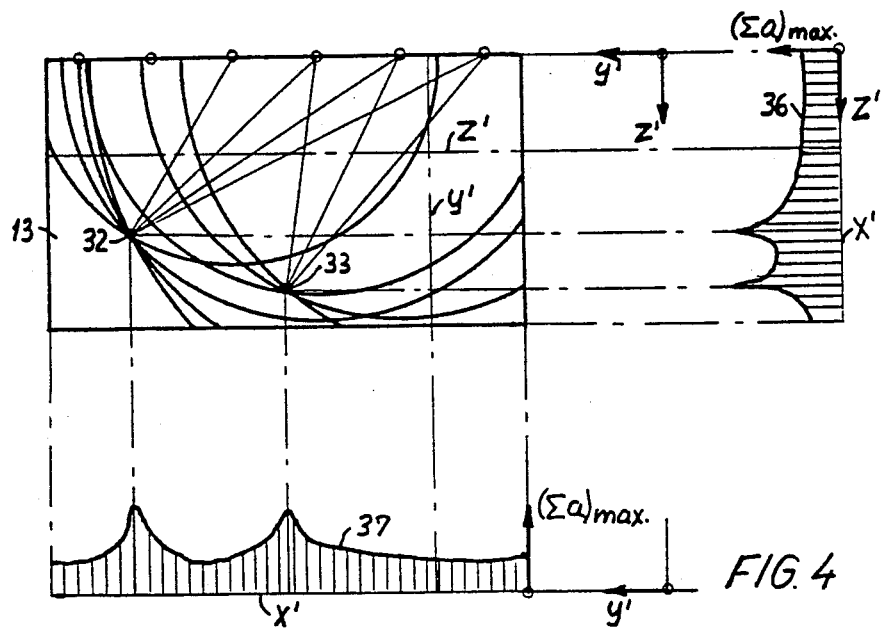
FIG. 4 is a schematic presentation of the storage and display of the sectional image of FIG. 3 after partial analysis by the method according to the present invention.

When all circular storage patterns intersecting at the location 31 have been eliminated, the remaining storage patterns in the second matrix memory 13 and the corresponding, revised video sectional image will now appear as illustrated schematically in FIG. 4. The circular storage patterns intersecting at the locations 32 and 33 have been kept intact during the elimination procedure described above, and the corresponding, less significant reflectors are not longer overshadowed by the high echo amplitude data values related to the more significant reflector at 31. This is more clearly shown by the curve 36, indicating the highest sums of amplitude data $((\Sigma a)_{max})$ stored in the lines z' of the matrix memory 13, and the curve 37, indicating the highest sums of amplitude data $((\Sigma a)_{max})$ stored in the columns y' of the matrix memory 13.

It is now possible to continue the analysis by successive elimination of the circular storage patterns intersecting at the locations 32 and 33, using the same echo signal elimination procedures as described above in relation to the first selected inhomogeneity at the location 31, and the analysis can be continued in this manner, until all echo signals contributing to flaw images in the video sectional image having amplitude values exceeding a predetermined noise threshold value have been eliminated from the totality of echo signals obtained during the examination of the object.

According to the invention, the method of analysing and evaluating can be further extended in the following manner:

Each time an actual echo pulse signal has been deleted from the first electronic memory during the elimination procedures described above, data representing the peak amplitude $(a_p)$ of the deleted echo pulse signal are stored at the storage address corresponding to the image pixel selected for elimination, in a third electronic matrix memory 38 identical with the second matrix memory 13 and having storage addresses (y",z") similarly adapted to store accumulated data representing echo amplitudes. When the elimination procedures relating to one or more inhomogeneities found in the selected sectional plane through the object examined have been terminated, a new video sectional image can be displayed, derived from the accumulated data $(\Sigma a_p)$ stored in the third matrix memory 38.

Figure 3:
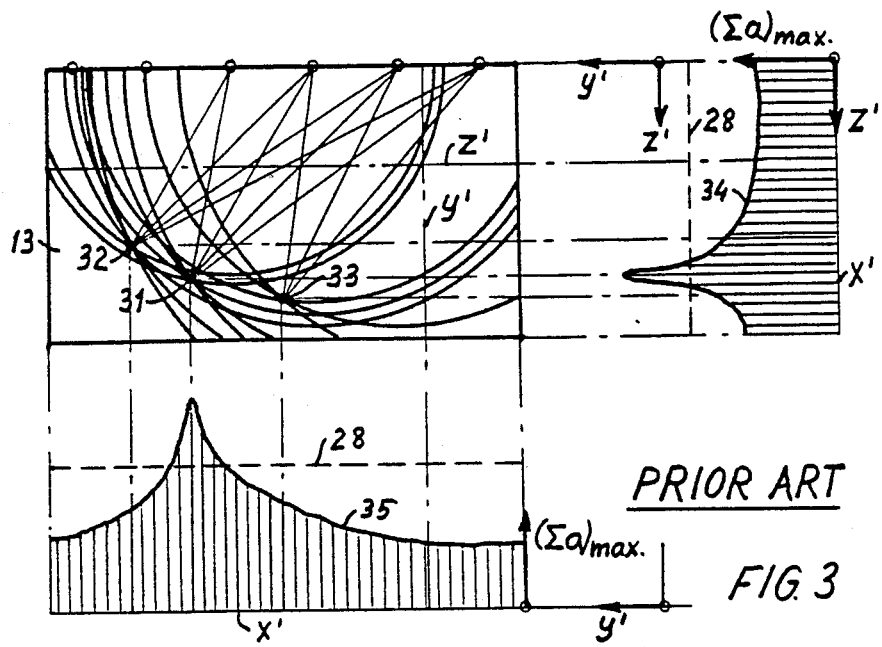
FIG. 3 is a schematic presentation of the storage and display of a second sectional image produced by the prior art system of FIG. 1.
Figure 5:
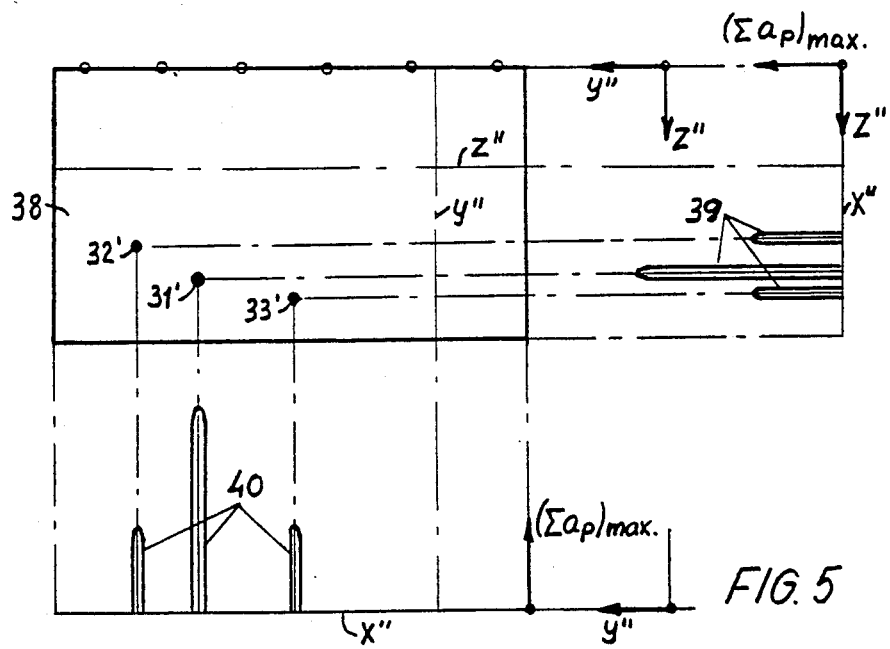
FIG. 5 is a schematic presentation of the storage and display of the sectional image of FIG. 4 after a completed analysis by the method according to the present invention.

Referring once more to the example illustrated in FIGS. 3 and 4, it it now assumed that all the circular storage patterns in the second matrix memory 13 intersecting at the locations 31, 32 and 33 have been eliminated as described above. The resulting storage patterns of accumulated peak amplitude data $(\Sigma a_p)$ in the third matrix memory 38 and the proportional video sectional image will now appear as illustrated schematically in FIG. 5.

It is clearly apparent that the complete elimination of noise and the exclusive storage of peak amplitude data at or near the locations 31', 32' and 33', corresponding to the true locations of the inhomogeneities in the selected sectional plane through the object, has led to a drastic improvement of the quality and precision of the flaw images produced by means of the analysing method according to the present invention. This improvement is even more clearly shown by the curve 39, indicating the highest sum of peak amplitude data $((\Sigma a_p)_{max})$ stored in the lines z" of the third matrix memory 38, and the curve 40, indicating the highest sums of peak amplitude data $((\Sigma a_p)_{max})$ stored in the columns y" of the third matrix memory 38.

According to the invention, the method of analysing and evaluating can finally be further extended in the following manner:

A number of parallel sectional planes 14,14a,14b, 14c is selected at predetermined mutual distances. For each selected sectional plane at a time, the echo pulse signal elimination and echo peak amplitude storage procedures are first performed as described above, resulting in a peak amplitude data storage pattern as described in the third matrix memory 38. Using the prior art system and procedures described above, the highest sums of peak amplitude data $((\Sigma a_p)_{max})$ 39,40 stored in each line z" and column y" are then transferred to the corresponding storage addresses in the appropriate lines or columns (x",y",z") in one or more electronic matrix memories 19,22,25, each memory being associated with a selected projection plane 20,23,26, and all storage addresses in the third matrix memory 38 are reset at zero value. When these procedures have been performed for all selected sectional planes 14,14a,14b,14c, it is possible to display one or more video projection images, derived from the totality of peak amplitude data stored in the corresponding matrix memories 19,22,25.

It will be apparent that the video projection images produced from the accumulated peak amplitude data stored in the third matrix memory 38 will show correspondingly improved flaw images, permitting equally improved flaw analysis and evaluation in three dimensions.

In actual practice, the prior art ultrasonic examinations will normally be performed on site by means of lightweight, hand-portable equipment, producing permanent, electronically readable records of the totality of connected position and echo pulse signals obtained during a thorough scanning of the interior of the object 2 from a great number of points of incidence 9 and in several difference directions of the central axis 6 of the sound beam. The final analysis and evaluation of the recorded data by the method according to the present invention can then be performed as a post processing procedure at any later time and at freely selectable noise and display threshold limits by means of standard personal computer equipment.

It will be understood that several modifications and variations of the method described may be applied without departing from the spirit and scope of the novel concepts of the present invention.

We claim:

1. A method of analyzing and evaluating the results of an ultrasonic examination by the pulse-echo method of a solid object having a plane or locally substantially plane surface, comprising the steps of:
   (a) moving at least one ultrasonic probe over the surface of the object, making said probe emit, at predetermined intervals of time, one short pulse of ultrasonic energy into the object,
   (b) producing at each emission of an ultrasonic pulse, digital position signals containing information on the corresponding position of the point of incidence and central axis direction of the sound beam in a predetermined three-dimensional system of co-ordinates in fixed relation to the object, (c) producing by means of ultrasonic equipment, on receipt of an echo pulse, digital echo signals containing information on the amplitude of said echo pulse, and on the length of the sound path from said point of incidence to the reflecting point causing said echo pulse, (d) storing by digital computing means, connected values of said echo and position signals in a first electronic memory, (e) selecting for study a sectional plane through the object examined, defining in said sectional plane a two-dimensional system of rectangular co-ordinates in known relation to said three-dimensional system of co-ordinates in the object examined, (f) determining for each echo pulse received, the circular curve of intersection, if any, between said sectional plane and a sphere having its center at the corresponding point of incidence of the sound beam and having as its radius the length of the sound path from said point of incidence to the reflecting point causing said echo pulse, (g) storing said echo signals by digital computing means in a second electronic matrix memory having storage addresses arranged in lines and columns associated with a corresponding network of lines and columns in said two-dimensional system of co-ordinates, each storage address being adapted to store data representing said echo amplitudes, and adapted, on receipt of a new data item, to add said new data item to the sum of data items previously stored at said storage address, by storing data representing each echo amplitude at all storage addresses located on the circle in said second matrix memory corresponding to said circular curve of intersection in said sectional plane.

(h) displaying by means of a video screen monitor, a video sectional image derived from the accumulated data stored in said second matrix memory, showing indications of inhomogeneities, if any, found in said sectional plane through the object examined, (i) establishing by digital computing means, a digital mathematical model simulating the shape, amplitude, directivity and progression of a sound pulse emitted by said ultrasonic probe from a selected imaginary point of incidence, said mathematical model being able to produce imaginary digital echo pulse signals from a selected imaginary point reflection source in the object examined, said imaginary echo pulse signals containing information on the amplitude of said imaginary echo pulse, and on the length of the sound path from said imaginary point of incidence to said imaginary point source causing said imaginary echo pulse, (j) selecting from said video sectional image of inhomogeneities found in the object examined, a first image-pixel at or near the flaw image of a first inhomogeneity, (k) introducing into said mathematical model a first imaginary point reflection source at the co-ordinates in the object examined corresponding to said select first image pixel, (l) introducing into said mathematical model a first combination of a first imaginary point of incidence and a first central axis direction of the sound beam, selected from among the combinations of actual position signals stored in said first electronic memory, (m) comparing the imaginary echo pulse signals obtained by said mathematical model with the corresponding actual echo pulse signals stored in said first electronic memory having amplitude values exceeding a predetermined threshold value, (n) deleting, in case of identical path length indicated by said imaginary and said actual pulse signals, said actual echo pulse signals from said first electronic memory, (o) successively introducing into said mathematical model the further combinations of points of incidence and central axis directions of the sound beam stored in said first electronic memory, (p) for each selected combination, repeating the steps (m) and (n) disclosed above in relation to said first combination, (q) producing a revised second video sectional image of inhomogeneities found in said sectional plane, derived from the remaining data stored in said first electronic memory, by repeating the steps (f), (g) and (h) disclosed above in relation to said first video sectional image, (r) successively selecting further image pixels remaining at or near the flaw image of said first inhomogeneity, (s) for each selected image pixel, repeating the steps (k), (l), (m), (n), (o), (p) and (q) disclosed above in relation to said first image pixel, until all echo signals contributing to the flaw image of said first inhomogeneity having amplitude values exceeding a predetermined threshold value have been eliminated from the totality of echo signals obtained during the examination of the object in question, (t) successively selecting from revised video sectional images, further flaw images of inhomogeneities found in said sectional plane through the object examined, and (u) repeating the steps (j), (k), (l), (m), (n), (o), (p), (q), (r), (s) and (t), until all echo signals contributing to flaw images in said revised video images having amplitude values exceeding a predetermined threshold value have been eliminated from the totality of echo signals obtained during the examination of the object in question.

2. The method according to claim 1, comprising for at least one selected inhomogeneity found in a selected sectional plane through the object examined, the further steps of:

(v) storing by digital computing means, each time an actual echo pulse signal has been deleted from said first electronic memory, data representing the peak amplitude of said actual echo pulse signals at the storage address corresponding to the image pixel selected for elimination, in a third electronic matrix memory identical with said second electronic matrix memory and having storage addresses similarly adapted to store accumulated data representing echo amplitudes, and (w) displaying by means of a video screen monitor, a revised video sectional image derived from the accumulated data stored in said third matrix memory, indicating echo information exclusively related to said selected inhomogeneity.

3. The method according to claim 2, comprising the further steps of:
  (x) selecting a number of parallel sectional planes through the object examined, at predetermined mutual distances,
  (y) storing by digital computing means, for each selected sectional plane, data representing the peak amplitudes of deleted actual echo pulse signals originating from inhomogeneities found in the object examined, and
  (z) displaying at least one video projection image on a selected projection plane in known relation to the object examined, said projection image being derived from the totality of peak amplitude data stored in relation to said parallel sectional planes.

* * * * *